United States Patent [19]
Raible

[11] Patent Number: 5,186,713
[45] Date of Patent: Feb. 16, 1993

[54] EXTRACORPOREAL BLOOD OXYGENATION SYSTEM AND METHOD FOR PROVIDING HEMOPERFUSION DURING TRANSLUMINAL BALLOON ANGIOPLASTY PROCEDURES

[75] Inventor: Donald A. Raible, Santa Ana, Calif.

[73] Assignee: Baxter International Inc., Deerfield, Ill.

[21] Appl. No.: 609,301

[22] Filed: Nov. 1, 1990

[51] Int. Cl.$^5$ ............................................. A61M 37/00
[52] U.S. Cl. ........................................ 604/4; 606/191; 606/194; 604/96
[58] Field of Search ........................................ 604/4–6, 604/96; 606/191, 194

[56] References Cited

U.S. PATENT DOCUMENTS

| | | | |
|---|---|---|---|
| 4,712,551 | 12/1987 | Rayhanabad . | |
| 4,848,344 | 7/1989 | Sos et al. | 606/194 |
| 4,862,891 | 9/1989 | Smith | 606/191 |
| 4,909,252 | 3/1990 | Goldberger | 606/194 |
| 4,917,667 | 4/1990 | Jackson | 604/96 |
| 4,921,478 | 5/1990 | Solano et al. . | |
| 4,921,483 | 5/1990 | Wijay et al. | 604/96 |
| 5,011,469 | 4/1991 | Buckberg et al. | 604/4 |
| 5,069,661 | 12/1991 | Trudell | 604/4 |

Primary Examiner—Robert A. Hafer
Assistant Examiner—Kerry Owens
Attorney, Agent, or Firm—Stetina & Brunda

[57] ABSTRACT

A method, device and system for providing a flow of oxygenated perfusion fluid (e.g. oxygenated whole blood) through a balloon angioplasty catheter to perfuse tissues which would normally be deprived of blood flow when the balloon of the angioplasty catheter is inflated. In accordance with the invention, an extracorporeal membrane oxygenation device is fluidly connected to the angioplasty catheter such that oxygenated fluid (e.g. oxygenated whole blood) may be passed through the catheter and caused to exit the catheter distal to the angioplasty balloon. The patient's own blood may be withdrawn, oxygenated by the extracorporeal membrane oxygenation device and subsequently reinfused through the angioplasty catheter. A dual-lumen introducer sheath may be employed for the dual function of a) facilitating insertion of the catheter and b) allowing withdrawal of blood for subsequent oxygenation and reinfusion through the angioplasty catheter.

39 Claims, 3 Drawing Sheets

EXTRACORPOREAL BLOOD OXYGENATION SYSTEM AND METHOD FOR PROVIDING HEMOPERFUSION DURING TRANSLUMINAL BALLOON ANGIOPLASTY PROCEDURES

FIELD OF THE INVENTION

The present invention relates generally to medical equipment and more particularly to an extracorporeal blood oxygenation system and method whereby a flow of oxygenated hemoperfusion blood is passed through the central lumen of a balloon angioplasty catheter to provide for perfusion of tissues (e.g. myocardial tissues) which are deprived of normal bloodflow when the angioplasty balloon is inflated.

Percutaneous transluminal angioplasty has become a commonly used procedure in the treatment of various obstructive disorders of the arterial circulation, including stenotic lesions of the coronary arteries, iliac arterial obstructions, femoropopliteal arterial obstructions, renal arterial obstructions, cerebrovascular arterial obstructions, coarctations of the aorta, stenotic arteries in transplant organs, stenotic saphenous vein bypass grafts, stenotic dialysis fistulas, stenotic portal systemic shunts and other obstructive vascular lesions.

The hemoperfusion device and system of the present invention is particularly useable in connection with transluminal coronary angioplasty procedures, and will be described herein with particular reference thereto. It will be appreciated, however, that the device and system of the present invention is broadly intended for use in connection with any and all types of angioplasty procedures, including but not limited to those specifically referred to above.

The usual technique for performance of percutaneous transluminal angioplasty procedures involves the initial insertion of a tubular introducer sheath or cannula into an appropriate artery (e.g. the femoral artery or axillary artery). An elongate, flexible angiocatheter, having at least one lumen running longitudinally therethrough, is then inserted through the lumen of the introducer sheath and is advanced, under fluoroscopic guidance, to a point near the stenotic lesion or obstruction to be treated. A guidewire is then passed through the lumen of the angiocatheter such that the distal tip of the guidewire emerges out of and beyond the distal tip of the angiocatheter. Thereafter, under continued fluoroscopic guidance, the tip of the guidewire is advanced through the stenotic lesion or obstruction. With the guidewire so positioned, the angiocatheter is then withdrawn and a balloon angioplasty catheter is subsequently advanced over the guidewire such that the balloon of the angioplasty catheter is adjacent the stenotic lesion or obstruction. Thereafter, the guidewire may be extracted and removed leaving the balloon angioplasty catheter positioned such that the balloon is adjacent the stenosis or occlusion. Thereafter, the balloon is repeatedly inflated with dilute radiographic contrast solution. Such inflation of the balloon brings about expansion of the offending stenotic lesion or obstruction. After the lesion or obstruction has been successfully expanded, the balloon is deflated and the balloon angioplasty catheter and introducer sheath are removed.

When transluminal balloon angioplasty is performed to alleviate a stenotic lesion or obstruction of a coronary artery, special care must be taken to ensure that adequate perfusion of the myocardium is maintained during the period(s) of time when the angioplasty balloon is inflated. This is particularly problematic because, in most angioplasty procedures, inflation of the balloon causes complete or nearly complete occlusion of the coronary artery in which it is positioned. Such occlusion of the coronary artery by the inflated balloon may deprive the myocardium of bloodflow to such extent that induction of arrhythmia and/or frank myocardial infarction may result.

Typically, in order to prevent the occurrence of iatrogenic myocardial infarction or hypoxically induced arrhythmia, it is common practice to periodically deflate and then reinflate the balloon during the angioplasty procedure. Such periodic deflation and reinflation of the balloon allows blood to flow around the balloon, thereby providing intermittent restoration of bloodflow to regions of the myocardium which lie distal to the location of the balloon. The performance of such periodic deflation and reinflation of the angioplasty balloon is a drawback in that it diminishes the efficiency of the balloon-expansion procedure. Also such repeated deflation/reinflation of the balloon increases the likelihood that occlusive complications will occur due to collapse and/or fragmentation of portions of offending atherosclerotic plaque.

In the event of occlusion due to collapse or fragmentation of offending atherosclerotic plaque, it is generally necessary to perform immediate cardiac surgery, by open tracheotomy, to accomplish coronary revascularization by traditional open-chest coronary bypass graft methods. The occurrence of such surgical emergency is life-threatening and extremely undesirable. Furthermore, in view of the potential for such occurrence, it is common practice to have a complete cardiovascular surgical team standing by during the performance of the balloon angioplasty procedure. The need for such stand-by surgical team greatly increases the cost of the angioplasty procedure.

Several methods and devices of the prior art have been intended to provide perfusion of blood deprived tissues during inflation of an angioplasty balloon, and to overcome the need for periodic deflation and reinflation of the balloon. Examples of such prior art methods and/or devices are described in U.S. Pat. Nos. 4,909,252 (Goldberger); 4,921,483 (Wijay et al.); and 4,917,667 (Jackson). However, such prior art methods and devices have not been routinely adopted by the medical profession and, indeed, the traditional process of periodically deflating and reinflating the totally occlusive angioplasty balloon during coronary angioplasty procedures has continued to be a standard practice in the art.

Accordingly, there exists a need in the art for improved methods and devices which are capable of providing adequate perfusion of tissues Which would normally be deprived of bloodflow during an occlusive angioplasty procedure.

SUMMARY OF THE INVENTION

The present invention overcomes some or all of the shortcomings of the prior art by providing a device, method and system whereby a flow of oxygenated perfusion fluid (e.g. oxygenated whole blood) may be infused through the lumen of an angioplasty catheter to bring about perfusion of tissues which would normally be deprived of bloodflow when the balloon of the angioplasty catheter is inflated.

In accordance with the present invention, there is provided an extracorporeal oxygenation device which is attachable to an angioplasty catheter to provide a flow of extracorporeally oxygenated fluid (e.g. oxygenated whole blood) through the angioplasty catheter. The extracorporeal oxygenation device is preferably sized and constructed to operate effectively with perfusion fluid flowing therethrough at 30 to 60 ml/min. In most coronary angioplasty applications, it is preferable that the extracorporeal oxygenation device be effectively operated with a perfusion fluid (e.g. blood) flow therethrough of about 45 ml/min., as such flow rate is typically compatible with the flow capacity of the coronary artery into which said perfusion fluid is infused in such coronary angioplasty applications.

Further in accordance with the present invention, there is provided an angioplasty system which comprises a) a balloon angioplasty catheter having a fluid passage lumen which opens distal to the balloon, b) an extracorporeal blood oxygenator, and c) a perfusion fluid source. The "perfusion fluid source" may be a source of whole blood, such as a cannula or needle which is insertable into the patient's own vasculature to permit withdrawal, oxygenation and reinfusion of autologous blood from the patient. The angioplasty catheter is positioned within the patient's vasculature at its desired operative position. The perfusion fluid source is connected to the inlet port of the extracorporeal blood oxygenation device and the outlet port of the extracorporeal blood oxygenation device is connected to the angioplasty catheter such that oxygenated perfusion fluid exiting the oxygenation device will pass through the angioplasty catheter and out of a distal opening formed in the angioplasty catheter, distal to the balloon. A pump or other fluid propulsion device is then used to cause perfusion fluid to flow from the perfusion fluid source, through the extracorporeal oxygenation device and through the fluid passage lumen of the angioplasty catheter so as to perfuse tissues lying distal to the catheter balloon.

Still further in accordance with the present invention, the "perfusion fluid source" component of the angioplasty system may comprise a dual lumen introducer sheath which is configured to serve the dual functions of a) facilitating insertion and placement of the angioplasty catheter and b) providing an apparatus through which blood may be withdrawn for subsequent passage through the extracorporeal oxygenation device and subsequent reinfusion through the angioplasty catheter. Such dual lumen introducer sheath comprises a first "introducer lumen" through which the angioplasty catheter may be introduced and advanced within the blood vessel and a second "blood withdrawal lumen" through which blood may be withdrawn while the angioplasty catheter remains disposed within the "introducer lumen".

Even further in accordance with the present invention, there is provided a method for performing transluminal balloon angioplasty procedures wherein an extracorporeal blood oxygenation device is utilized to provide a flow of oxygenated perfusion fluid (e.g. oxygenated whole blood) through an angioplasty catheter during the angioplasty procedure.

Various and further objects and advantages of the present invention will become apparent to those skilled in the art upon reading and understanding the following detailed description and the accompanying drawings.

DETAILED DESCRIPTION OF THE PREFERRED EMBODIMENT

The following detailed description and the accompanying drawings are provided for purposes of illustrating and describing presently preferred embodiments of the invention and are not intended to limit the scope of the invention in any way.

i. A Preferred Membrane Oxygenator Device

Figures 1, 2:
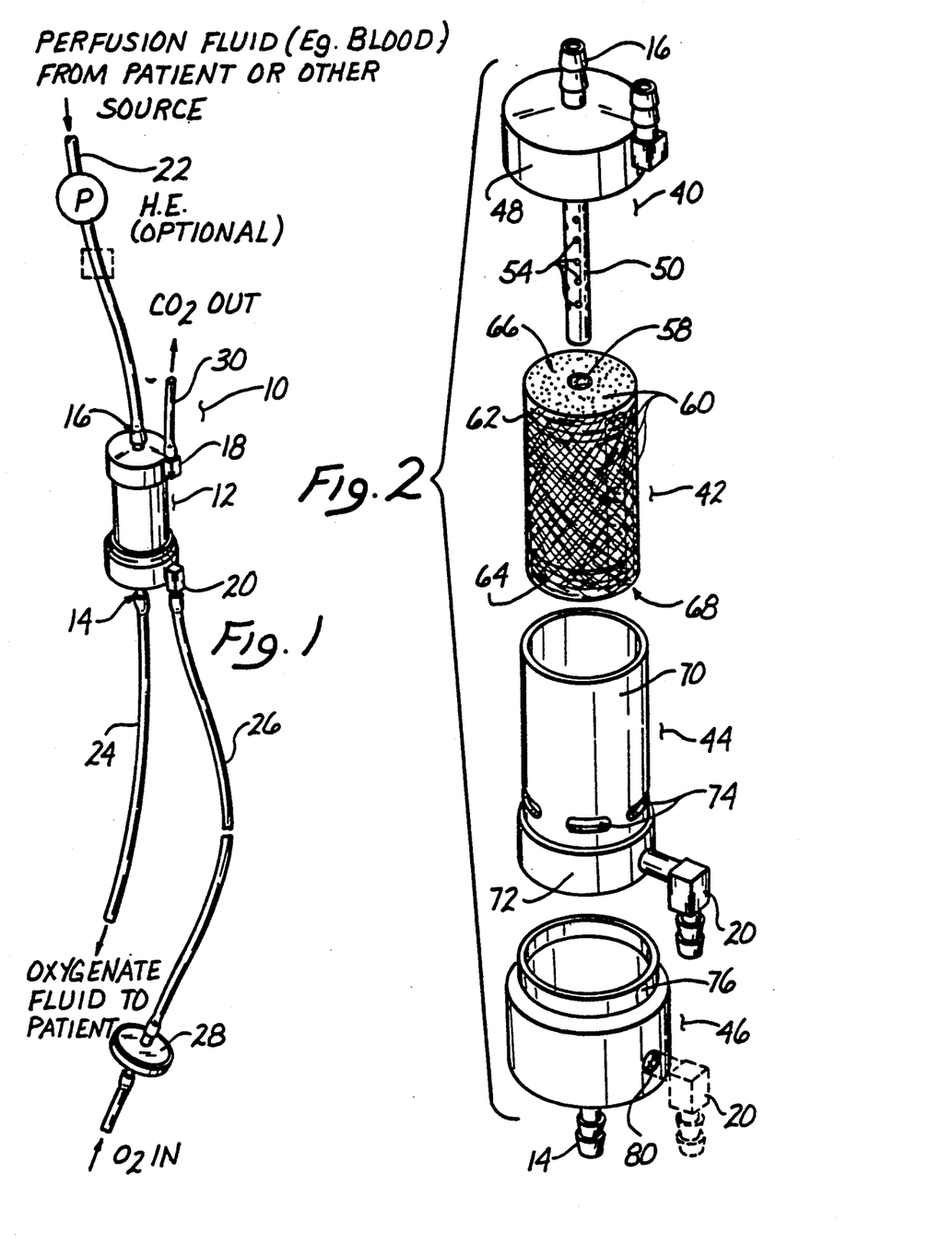
FIG. 1 is a perspective view of a presently preferred blood oxygenator assembly of the present invention.
FIG. 2 is an exploded view of the membrane oxygenator component of the extracorporeal blood oxygenator assembly shown in FIG. 1.

As shown in FIG. 1, the presently preferred blood oxygenator assembly 10 of the present invention comprises a membrane oxygenator device which is approximately three inches in length (not including inlet/outlet connectors 14, 160) and approximately two inches in diameter. The preferred membrane oxygenator device is sized to operate effectively at fluid rates which do not exceed the flow capacity of the blood vessel into which the perfusion fluid is being infused. For coronary angioplasty procedures, the membrane oxygenator device is preferably sized and constructed to operate effectively with fluid (e.g. blood) flow therethrough at 30 to 60 ml/min. and preferably at about 45 ml/min., as such flow rate can generally be accommodated by the coronary artery into which the perfusion fluid (e.g. blood) is being infused. The device 12, as shown, incorporates having a blood inlet 16, a blood outlet 14, a gas inlet 20 and a gas outlet 18. A blood supply tube 22 is fluidly attached to a blood withdrawal device, such as a needle or other percutaneously insertable conduit positioned with the patient's vasculature. A pump may be positioned on tube 22 so as to pump blood from the patient's vasculature, through blood supply tube 22 and into the membrane oxygenator component 12. A blood return tube 24 is connected to the blood outlet 14 of the membrane oxygenator component 12. The blood return tube 24 is attachable to the proximal end of a balloon angioplasty catheter having a perfusion supply lumen extending therethrough, so as to provide a flow of hemoperfusion blood from the membrane oxygenator component 12, through the perfusion supply lumen and out of the distal portion of the catheter, distal to the occlusive angioplasty balloon.

A gas supply tube 26 is connectable to the gas inlet 20 of the membrane oxygenator component 12 so as to provide a flow of oxygenated gas into and through the hollow fiber membranes within membrane oxygenator component 12. A gas outlet vent tube 30 is connected to the gas outlet port 18 of the membrane oxygenator component 12 so as to provide for venting of $CO_2$ and residual oxygen-containing gas from the upper gas chamber or gas outlet space 86. Antibacterial or microbiostatic filter 28 (Bentley GFTM bidirectional filter, Baxter Healthcare Corporation, Bentley Laboratories Division, Irvine, Calif.) is positionable, as shown, on the gas inlet tube 26 so as to capture or filter out potentially pathogenic microorganisms and/or particulates prior to passage of the oxygen-containing gas into the membrane oxygenator device 12 of the present invention.

The membrane oxygenator component 12 is relatively small in size (e.g. external dimension of approximately 3 inches in length and approximately 2 inches in diameter) compared to the typical membrane oxygenation devices of the prior art, such as those routinely used to maintain whole body perfusion of patients during cardiopulmonary bypass. Such small size of the membrane oxygenator component 12 of the present invention permits the membrane oxygenator component 12 to function with a comparatively small extracorporeal blood volume during priming and operation. Because the membrane oxygenator 12 is sized to minimize the extracorporeal blood volume required for operation, the device of the present invention is usable with a relatively small blood supply flow, as may be obtained through a simple needle or other conduit which has been percutaneously inserted into a peripheral artery (e.g. femoral artery). Furthermore, such minimization of the amount of blood extracted into the extracorporeal circuit is important to the clinical stability of the patient who is undergoing the angioplasty procedure.

Figures 3, 6, 7:
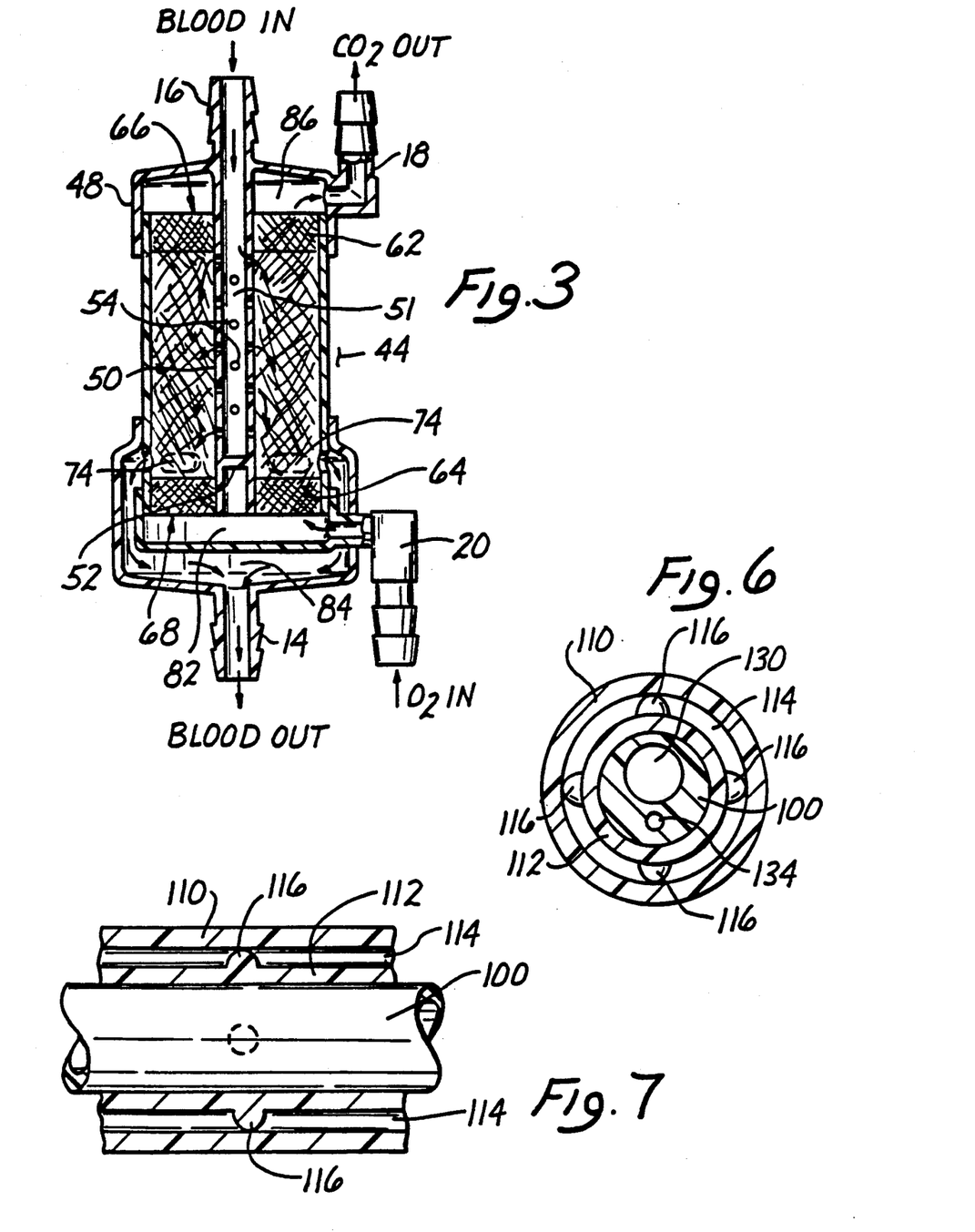
FIG. 3 is a vertical cross-sectional view of the membrane oxygenator component of the extracorporeal blood oxygenator assembly shown in FIG. 1.
FIG. 6 is a cross-sectional view through line 6—6 of FIG. 4.
FIG. 7 is a longitudinal sectional view through line 7—7 of FIG. 4.

The functional components of the presently preferred membrane oxygenator device 12 may be segregated into four (4) basic portions, i.e. an upper assembly 40, a spiral wrapped hollow fiber membrane assembly 42, a middle shell assembly 44 and a lower assembly 46.

The upper assembly 40 comprises a generally rigid lid or cap 48 assembly having the blood inlet connector 16 extending through the top side thereof. The blood inlet connector 16 is directly attached to and fluidly consistent with a hollow inner bore 51 formed within a generally cylindrical perforated core 50. Core 50 extends downwardly from the mid-region of the underside of the cap member 48. A bulkhead 52 is formed at the base of the inner bore 51 of core 50 so as to fully block the inner bore or lumen of the core 50, thereby forming a blind end at the bottom of the core 50. One or more of blood outflow apertures 54 are formed in the lateral sidewall of the core 50, above the bulkhead 52. Such blood outflow apertures 54 provide for multidirectional out passage of blood from the inner lumen or hollow inner bore of the core 50.

The core 50 is preferably of generally cylindrical configuration although various other configurations (e g. rectangular, bulbous, ovoid) may also be used. In the embodiment shown, the cross-sectional diameter of the core 50 between ¼ inch and ¾ inch and preferably about ½ inch.

The core 50 is positioned within the central passage of the spiral wrap hollow fiber membrane assembly 42. The hollow fiber membranes 60 are spirally wrapped around the core 50 such that the hollow fiber membranes 60 are disposed within the inner chamber formed inside the cylindrical body 70, beneath the upper potting structure 62 and above the lower potting structure 64. The inner diameter of the cylindrical body is about ¼ inch to 1¾ inch and preferably about ½ inches. The linear distance between the top of the lower potting structure 64 and the underside of the top potting structure 62 is about 1 inch to ½ and preferably about ⅛ inch.

Each individual hollow fiber membrane 60 comprises a tubular membrane having pores of preferably about 300-400 microns in diameter formed therein. As blood passes out of the outflow apertures 54 and circulates over the outer surfaces of the hollow fiber membranes 60, such membrane will permit oxygen to diffuse outwardly from the lumens of the hollow fiber membranes 60, through the pores formed therein. Also, carbon dioxide will diffuse inwardly from the blood, thereby providing for the derived $O_2/CO_2$ gas exchange.

The middle shell assembly 44 comprises a cylindrical body 70 having a basal cap member 72 mounted on the bottom end thereof.

Blood passing out of the blood outflow apertures 54 will pass over and come in contact with the exterior surfaces of a multiplicity of hollow fiber membranes 60 which are spirally or otherwise arranged around the central passageway 58.

The hollow fiber membranes 60 may be arranged within the inner chamber in any manner that provides for the desired gas exchange function of the device. In the preferred embodiment, the hollow fiber membranes 60 are spirally wrapped or wound about a central vertical axis within the inner chamber, at angles ranging from 30 to 90 degrees, relative to such central vertical axis. Such spiral wrapping or winding of the fibers results in the fibers crossing over one another, in opposite directions, with each wrap. The angles at which the membranes are wound relative to the central axis may be constant or varied from one wrap to another, in such manner as to facilitate the desired flow of blood over the outer surfaces of the hollow fiber membranes 60 and the desired occurrence of gas exchange when such bloodflow takes place. In the preferred embodiment shown, the hollow fiber membranes are spirally "filament" wound at opposite angles of about 65 degrees relative to the central vertical axis of the device. The upper ends of the hollow fiber membranes 60 are inserted and encased within the upper potting structure 62 while the lower ends of the hollow fiber membranes are inserted and encased within the lower potting structure 64. The upper surface 66 of the upper potting structure 62 and the lower surface 68 of the lower potting structure 64 are cut in generally horizontal planes such that the upper and lower ends of the tube-like hollow fiber membranes 60 will open into upper gas chamber 86 through the upper surface 66 of the upper potting structure 62 and into lower gas chamber 82 through the lower surface 68 of the lower potting structure 64. By such arrangement, fluid (e.g. oxygen-air mixture) may enter the inner lumens of the hollow fiber membrane 60 through the lower gas chamber 82 on the underside 68 of the lower potting structure 64 and may subsequently pass upwardly through the inner lumens of the hollow fiber membranes 60 and out of the upper ends of the hollow fiber membranes 60, flowing into the upper gas chamber 86 on the upper side 66 of the upper potting structure 62 and subsequently out of gas outlet 18.

The individual hollow fiber membranes 60 comprise a multiplicity of individual, tube-like gas permeable hollow fiber membranes of the type commonly used in extracorporeal membrane oxygenation system, The basal cap member 72 is sealed to the outer surface of cylindrical wall 70 such that, when the hollow fiber membrane assembly 42 is operatively mounted within the interior of the middle shell assembly 44, there will exist a generally fluid tight gas entry space or lower gas chamber 82 beneath the underside of the lower potting structure 64 and above the bottom surface of the basal cap member 72 Upon final assembly of the device, the gas inlet fitting 20 is inserted through an aperture and is inserted into and adhesively bonded, or otherwise fixed and sealed to the basal cap member 72 so as to provide a fluid carrying pathway into and/or out of the lower gas chamber 82.

The bottom assembly 46 fits over the lower portion of the middle shell assembly 44 and the upper rim 76 of the bottom assembly 46 is fused to the outer surface of the cylindrical body 70 of the middle shell assembly 44 above blood outflow slots 74. The bottom assembly 46 is sized and configured to define an inner blood receiving cavity 84 therewithin such that blood flowing out of the slots 74 of the middle shell assembly 44 may enter the upper region of the blood receiving cavity 84 and may drain downwardly therein, through the blood outlet port 14.

A separate optional heat exchanger (H.E.) or blood warmer may be positioned on either the blood inlet line 22, blood outlet line 24 or may be incorporated within the body of the membrane oxygenator component 12. It is preferable that the heat exchanger H.E. be positioned on the blood inlet line 22. Also, the heat exchanger H.E. may comprise one or more heatable or coolable members (e.g. heat exchange tubes or coils) positioned within the inner chamber so as to come in contact with the blood passing through the membrane oxygenator component 12.

For example, one or more small diameter heat exchange tubes may extend vertically adjacent the perforated core 50 such that blood exiting the perforated core 50 through apertures 54 will come in contact with the heat exchange tubes prior to passing through the network of spirally wrapped hollow fiber membranes 60. Such heat exchange tubes may comprise a plurality of small diameter linear tubes arranged on the outside of the core 50 or, alternatively, may comprise a single small diameter tubular coil wound around the outside of the core 50. Such heat exchange tube(s) may be connected to an external source of temperature controlled liquid such that the temperature controlled liquid will flow through the tube or tubes, preferably in a recirculating manner. Thus, by such arrangement, a functional heat exchange or temperature control element may be incorporated into the membrane oxygenator component 12 of the present invention.

ii Method of Operation of the Preferred Membrane Oxygenator Device

In normal operation, the membrane oxygenator 12 of the present invention is positioned near the body of the patient, and may be connected by way of a suitable connector or clamp, to a vertical support member such as an intravenous pole or the like. The oxygen inlet port 20 is connected to a source of oxygenated gas such that the oxygenated gas will flow inwardly through inlet port 20, into the lower gas chamber 82, and subsequently upwardly through the hollow inner lumens of the hollow fiber membrane 60. Thereafter, the gas will exit the upper ends of the hollow lumens of the hollow fiber membranes 60, into upper gas chamber 86 and will subsequently flow outwardly through gas outlet port 18.

While the above description indicates gas flow upwardly from the bottom to the top of the membrane oxygenator component 12, it will be appreciated that flow may also be effected in the opposite direction (i.e. entering through the top gas chamber 86, passing downwardly through the lumens of the hollow fiber membrane 60 and subsequently exiting through bottom chamber 82).

Furthermore, it will be appreciated that the membrane oxygenator component 12 need not be operated in a vertical position and, in fact, may be positioned horizontally or on an angle. Thus, the top gas chamber 86 and bottom gas chamber 82 may, in actuality, exist as right and left lateral gas chambers, being horizontally or otherwise juxtaposed to one another with the hollow fiber membrane 60 extending therebetween.

The blood inlet port 16 will be connected to a blood withdrawal apparatus fluidly connected to the patient's vascular or other blood source, such as a bag or container of whole blood or other special red fluids. A pump (e.g. a peristaltic centrifugal roller type or ventricular blood pump) will be employed to pump blood through blood inlet 16 and down the inner lumen of the blood inlet conduit 50 such that the blood will flow outwardly through outflow ports 54. Blood flowing out of ports 54 will pass downwardly over the exterior surfaces of the hollow fiber membranes 60, thereby undergoing $CO_2/O_2$ gas exchange in accordance with standard membrane oxygenation principles. The amount of gas exchange which takes place and the resultant $Po_2$ and $PCO_2$ of the blood will be controlled, and may be varied in accordance with standard membrane oxygenation techniques routinely utilized in the art. In most angioplasty applications, it will be desirable to raise the $Po_2$ of the blood well above that of normal arterial blood (i.e. normal arterial $Po_2 = 75-100$ mm Hg). Upon reaching the bottom region of the hollow fiber assembly 42, the oxygenated blood will pass outwardly through slots 74, into blood collection space 84. The blood will then drain downwardly through blood collection space 84 and out of blood outlet 14. The blood outlet 14 is fluidly connected to the proximal portion of an angioplasty catheter such that blood flowing out of the oxygenator will pass through a lumen (e.g. the guidewire lumen or a dedicated perfusion lumen) of the angioplasty catheter and will exit the angioplasty catheter through one or more outlet ports located distal to the angioplasty balloon, thereby providing a flow of oxygenated hemoperfusion blood to tissues which normally would be deprived of bloodflow when the angioplasty balloon is inflated.

Although the above description describes the blood passing in the top and out of the bottom of the membrane oxygenator component 12, it will be appreciated that, alternatively, the membrane oxygenator 12 may be positioned in various other orientations, including orientations whereby the blood will enter the bottom and exit the top of the device and/or orientations wherein the blood will enter one side and exit the opposite side of the device.

iii. A Preferred Angioplasty/Hemoperfusion System

In accordance with the present invention, there is also provided an angioplasty/hemoperfusion system as illustrated in FIGS. 4–7.

As shown, the presently preferred angioplasty/hemoperfusion system of the present invention incorporates a) a membrane oxygenator device such as the above-described membrane oxygenator assembly 10, along with b) an angioplasty balloon catheter 100 and c) a specialized dual-lumen introducer sheath 102.

Figure 5:
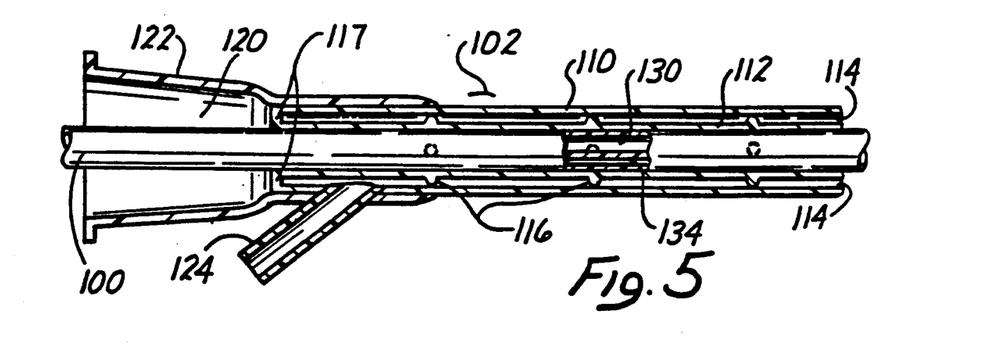
FIG. 5 is a sectional view of the presently preferred dual lumen introducer sheath shown in FIG. 4, with a balloon angioplasty catheter operatively inserted therethrough.

The dual lumen introducer sheath 102 comprises an outer tube 110 having an inner tube 112 disposed coaxially therewithin. The outer diameter of the inner tube 112 is smaller than the lumen diameter of the outer tube 110 so as to define an annular blood withdrawal space 114 therebetween. In the embodiment shown, a plurality of lugs or spacing members 116 are formed on the outer surface of the inner tube 112 and register against or are connected to the inner surface of the outer tube 110 so as to maintain the inner tube 112 in substantially fixed spacial relation to the inner surface of the outer tube 110. The annular space 114 defined between the outer surface of the inner tube 112 and the inner surface of the outer tube 110 will be generally constant about its entire diameter. The lugs or spacing members 116 need not necessarily be in the configuration of individual lugs or spacing members 116, as shown, but rather may comprise any type of spacing or registry structures capable of maintaining relatively fixed positioning of the inner tube 112 within the outer tube 110. For example, the inner tube 112 and/or outer tube 110 may incorporate one or more extruded or molded ribs on the outer surface of the inner tube 112 and/or inner surface of the outer tube 110. Similarly, there are other types of individual registry members which may be utilized to achieve the desired spacing between the inner tube 112 and outer tube 110 such that blood may be withdrawn in a proximal direction through the blood Withdrawal space 114.

The blood withdrawal space 114 terminates proximally against bulkhead 117 which is formed about the base of the inner bore 120 of the Leur hub 122 of the introducer 102. A blood withdrawal side arm 124 is fluidly connected to the proximal region of the blood withdrawal space 114 so as to provide for continuous or intermittent withdrawal of blood through the blood withdrawal space 114. A stopcock 115 is provided to enable the operator to selectively open and close bloodflow through sidearm 124.

Figure 4:
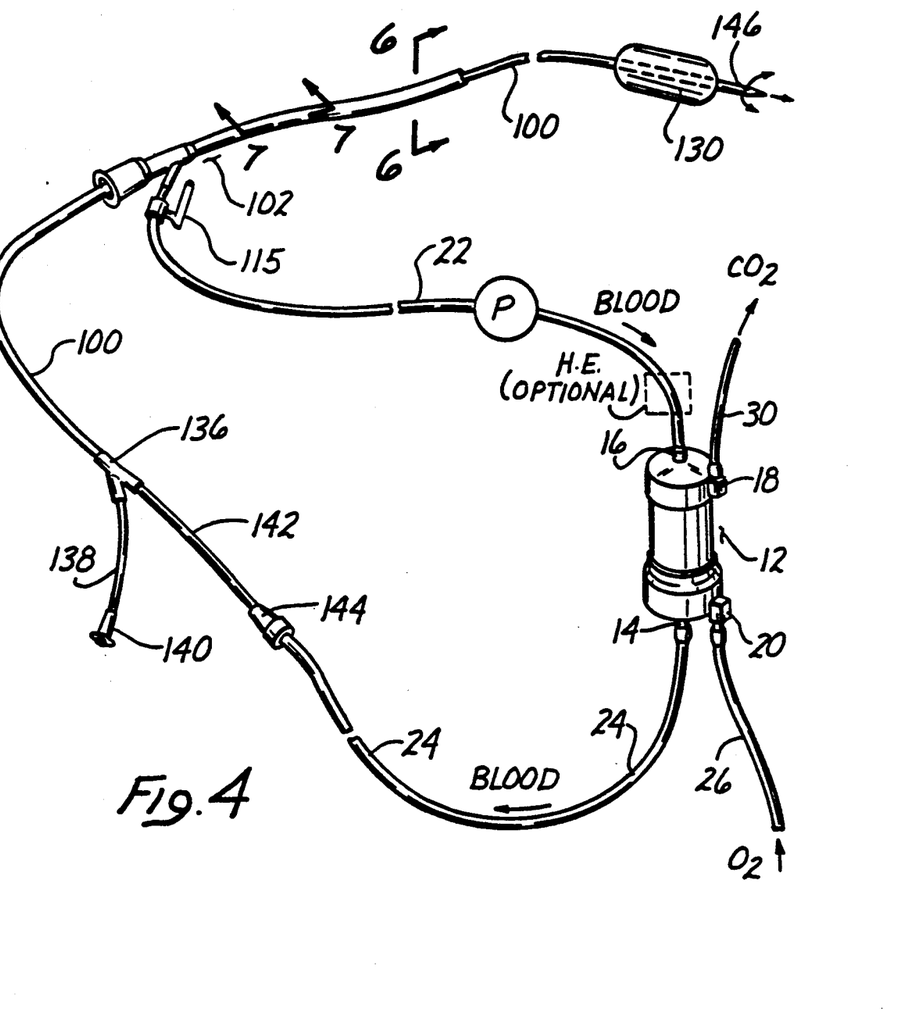
FIG. 4 is a perspective view of a presently preferred system for providing oxygenated hemoperfusion blood during performance of a transluminal balloon angioplasty procedure.

The angioplasty catheter 100 comprises a generally elongate flexible catheter body having a first guidewire/perfusion fluid lumen 130 extending longitudinally therethrough and a second balloon inflation lumen 134 also extending longitudinally therethrough. The balloon inflation lumen 134 is fluidly connected at its proximal end to the balloon inflation side arm 138, and is fluidly connected at its distal end to the interior of the balloon 132. Thus, a syringe containing dilute radio-opaque liquid or other balloon inflation fluid may be attached to the Leur connector 140 on the proximal end of the balloon inflation lumen side arm 138 and the radio-opaque liquid or other balloon inflation fluid may be thereby infused or injected through the balloon inflation fluid lumen 134 and into the interior of the balloon 132, causing inflation thereof.

The guidewire/perfusion fluid lumen 130 extends longitudinally through the body of the catheter and is fluidly connected at its proximal end to the guidewire/perfusion fluid inlet arm 142.

iv. Method of Operation of the Preferred Angioplasty/Hemoperfusion System

In the performance of standard transluminal angioplasty procedures, the balloon angioplasty catheter 100 is inserted over a prepositioned guidewire, through the inner lumen of the inner tube 112 of the introducer 102, as shown. The inner tube 112 is sized relative to the angioplasty balloon catheter 110 such that the outer surface of the angioplasty balloon catheter is generally slidably positioned against the inner surface of the inner tube 112 so as to permit slidable advancement and withdrawal of the angioplasty catheter through the interior of the inner tube 112. The slidable contact of the outer surface of the angioplasty catheter 100 with the inner surface of the inner tube 112 establishes a generally fluid tight seal therebetween, thereby preventing backflow of blood around the angioplasty catheter 100.

After the catheter has been advanced to its operational position within the body (i.e. such that the balloon 132 is adjacent the lesion or occlusion to be treated) the prepositioned guidewire is extracted from the guidewire/perfusion fluid lumen 130. Thereafter, the blood outlet line 24 of the membrane oxygenator 12 is connected to the Leur connector 144 of the guidewire/perfusion fluid inlet arm 142, as shown. Similarly, the blood withdrawal tube 22 is connected to the blood withdrawal side arm 124 of the dual lumen introducer sheath 102.

A source of filtered, oxygenated gas is connected to gas inlet tube 26 so as to cause a flow of oxygen through the inner lumens of the hollow fiber membranes 60 positioned within the membrane oxygenator 12.

Stopcock 115 is then opened and pump P is actuated to provide a continual withdrawal flow of blood through the blood withdrawal lumen 114 of the dual lumen introducer sheath 102, through side arm 124, through the tube 22 and into the membrane oxygenator 12. The blood will thereby flow over and in contact with the hollow fiber membranes 60 positioned within the membrane oxygenator 12 and will be oxygenated, and will give up carbon dioxide, in accordance with standard membrane oxygenation techniques. Thereafter, the blood with flow out of blood outlet 14, through blood return line 24, through the guidewire/ perfusion fluid lumen 130 of the catheter and out of a plurality of sidewall apertures 146 located near the distal tip of the catheter, distal to the balloon 130.

By such arrangement, the system of the present invention provides for continuous withdrawal, oxygenation and reinfusion of the patient's own blood.

It will be appreciated that one or more injection ports may also be provided on the blood return line 24 and/or the blood withdrawal line 22 for addition of any desired fluids or medicaments such as anticoagulants and/or vasodilators and/or antiarrhythmic drugs.

It will be further appreciated that the membrane oxygenator component 12 need not be positioned in a vertical orientation, as shown, and may be mounted in a horizontal orientation or any other position whereby the operative flow of blood and gas is maintainable.

Additionally, the membrane oxygenator component 12, as described above, is constructed such that gas flow through the hollow fiber membrane 60 may occur in either direction. Thus, in the preferred embodiment shown in the drawings, the gas flow enters through the bottom of the membrane oxygenator component 12 and exits through the top thereof. Alternatively, however, it would be possible to have the oxygenated gas enter the top of the membrane oxygenator component 12 and to thereafter exit through the bottom thereof.

The invention has been described herein with specific reference to presently preferred embodiments thereof. Those skilled in the art will recognize that various additions, modifications, deletions and alterations may be made to such preferred embodiments without departing from the spirit and scope of the invention. For example, in the hemoperfusion method and system described herein, the preferred dual lumen introducer sheath need not be employed and, in fact, the perfusion blood may be extracted from a separate blood vessel, different from the blood vessel into which the angioplasty catheter is inserted, and may be withdrawn through any standard blood withdrawal apparatus such as a percutaneously inserted needle or flexible intravenous catheter. Furthermore, the source of hemoperfusion fluid need not be the patient's own blood but, rather, may comprise a separate container of non-autogenous blood or a source of another liquid capable of carrying oxygen such as presently or hereafter oxygen-carrying perfusion solutions (e.g. fluorocarbon solutions). Accordingly, it is intended that any and all foreseeable modifications, additions, deletions and alterations to the described embodiments be included within the scope of the following claims.

What is claimed is:

1. A method of providing a flow of extracorporeally oxygenated perfusion fluid through a balloon angioplasty catheter inserted into an artery of a patient whose heart and lungs are functioning absent extracorporeal cardiopulmonary support, said method comprising the steps of:
   a) passing a perfusion fluid through an extracorporeal membrane oxygenation device such that the perfusion fluid will become oxygenated thereby; and, subsequently,
   b) passing the oxygenated perfusion fluid through the catheter lumen and causing the oxygenated perfusion fluid to exit the catheter distal to the angioplasty balloon.

2. The method of claim 1 wherein step (a) comprises pumping whole blood through said extracorporeal oxygenation device and subsequently through the catheter lumen.

3. The method of claim 1 wherein step (a) further comprises:
   inserting a blood withdrawal apparatus into a blood vessel of the patient upon whom the angioplasty procedure is to be performed;
   fluidly connecting the blood withdrawal apparatus to the extracorporeal oxygenation device; and
   withdrawing blood from the blood vessel and passing the withdrawn blood through the extracorporeal oxygenation device and subsequently through the lumen of the catheter.

4. The method of claim 1 wherein step (a) comprises:
   percutaneously inserting an intravascular cannula into a peripheral blood vessel of the patient;
   fluidly connecting the intravascular cannula to the extracorporeal oxygenation device such that blood may pass from the patient into the extracorporeal oxygenation device; and
   withdrawing blood from the intravascular cannula and passing said withdrawn blood through the extracorporeal oxygenation device and thereafter through the lumen of the catheter.

5. A method of providing a flow of extracorporeally oxygenated blood through a balloon angioplasty catheter, said method comprising the steps of:
   inserting a dual lumen introducer sheath into a blood vessel, said dual lumen introducer sheath having a first catheter introducer lumen for insertion of the angioplasty catheter therethrough and a second blood withdrawal lumen for withdrawal of blood therethrough;
   inserting an angioplasty catheter into the vasculature of the patient through the catheter introducer lumen of the dual lumen introducer sheath;
   fluidly connecting the blood withdrawal lumen of the dual lumen introducer sheath to an extracorporeal membrane oxygenation device;
   withdrawing blood from the blood vessel through the blood withdrawal lumen and passing the withdrawn blood through the extracorporeal oxygenation device for oxygenation therein; and
   passing the oxygenated blood through a lumen of the catheter and causing the oxygenated blood to exit the catheter distal to the angioplasty balloon.

6. The method of claim 1 further comprising the step of:
   adjusting the temperature of the fluid prior to passage of the fluid through the lumen of the catheter.

7. The method of claim 6 wherein the step of adjusting the temperature of the fluid prior to passage of the fluid through the lumen of the catheter comprises:
   positioning a heat exchange apparatus proximate said extracorporeal oxygenation device such that perfusion fluid will come in contact with said heat exchange apparatus before passing through said extracorporeal oxygenation device.

8. The method of claim 6 wherein the step of adjusting the temperature of the fluid prior to passage of the fluid through the lumen of the catheter comprises:
   positioning a heat exchange apparatus within said extracorporeal oxygenation device such that the perfusion fluid will come in contact with said heat exchange apparatus while passing through said extracorporeal oxygenation device.

9. The method of claim 3 wherein the step of inserting a blood withdrawal apparatus into a blood vessel of a patient upon whom the angioplasty procedure is to be performed comprises:
   inserting a blood withdrawal apparatus into a peripheral artery of the patient upon whom the angioplasty procedure is to be performed.

10. The method of claim 3 wherein the step of inserting a blood withdrawal apparatus into a blood vessel of a patient upon whom the angioplasty procedure is to be performed comprises:
    percutaneously inserting an intravascular cannula into a peripheral blood vessel of the patient upon whom the angioplasty procedure is to be performed.

11. The method of claim 3 wherein the step of inserting a blood withdrawal apparatus into a blood vessel of a patient upon whom the angioplasty procedure is to be performed comprises:
    inserting an intravascular cannula into a femoral artery of the patient upon whom the angioplasty procedure is to be performed.

12. The method of claim 3 wherein the step of inserting a blood withdrawal apparatus into a blood vessel of a patient upon whom the angioplasty procedure is to be performed comprises:

inserting an intravascular cannula into the axillary artery of a patient upon whom the angioplasty procedure is to be performed.

13. The method of claim 1 further comprising the step of:
controlling the rate at which blood is withdrawn from the blood vessel so that the rate at which blood is withdrawn does not to exceed the available volume of blood flowing through the blood vessel.

14. The method of claim 1 wherein step (a) further comprises:
passing said perfusion fluid through the extracorporeal oxygenation device at a rate of 30-60 ml/min.

15. The method of claim 1 wherein step (a) further comprises:
passing said perfusion fluid through the extracorporeal oxygenation device at a rate of about 45 ml/min.

16. The method of claim 13 wherein the step of controlling the rate at which perfusion fluid flows through the lumen of the catheter comprises maintaining the flow rate of said perfusion fluid through the lumen of said catheter at 30-60 ml/min.

17. The method of claim 13 wherein the step of controlling the rate at which perfusion fluid flows through the lumen of the catheter comprises maintaining said rate at approximately 45 ml/min.

18. A method of performing transluminal balloon angioplasty in an artery of a patient whose heart and lungs are functioning absent extracorporeal cardiopulmonary support, using a balloon angioplasty catheter which has a proximal end, a distal end, at least one lumen extending therethrough and an opening distal to the balloon to permit fluid passing through the lumen to exit the catheter distal to the balloon, said method comprising:
a) inserting the distal end of said angioplasty catheter into a blood vessel and advancing said angioplasty catheter such that the balloon is positioned in its desired operative position;
b) inserting an intravascular cannula into a blood vessel of the patient to withdraw blood therefrom;
c) providing an extracorporeal blood oxygenation device having a blood inlet and a blood outlet;
d) fluidly connecting the intravascular cannula to the blood inlet of the extracorporeal blood oxygenation device;
e) fluidly connecting the blood outlet of the extracorporeal blood oxygenation device to the lumen of the angioplasty catheter; and
f) withdrawing blood through the intravascular cannula and pumping the withdrawn blood through the extracorporeal oxygenation device such that the blood will become oxygenated by the oxygenation device and will subsequently flow through the lumen of the catheter and out of the distal opening thereof.

19. The method of claim 18 wherein step (c) further comprises:
providing an extracorporeal blood oxygenation device which is sized and constructed to operate effectively with blood flowing therethrough at a rate of 30-60 ml/min.

20. The method of claim 18 wherein step (f) further comprises:
controlling the rate at which blood is pumped through the extracorporeal blood oxygenation device such that said rate is between 30 and 60 ml/min.

21. The method of claim 18 wherein step (d) further comprises:
providing an extracorporeal blood oxygenation device which is sized and constructed to operate effectively with blood flowing therethrough at a rate of 30-60 ml/min.

22. The method of claim 18 further comprising the step of:
adjusting the temperature of the blood prior to passage of the blood through the lumen of the catheter.

23. The method of claim 18 wherein step (b) comprises:
inserting an intravenous needle into a peripheral blood vessel of the patient to withdraw blood therefrom.

24. The method of claim 18 wherein step (b) comprises:
inserting a flexible intravascular cannula into a blood vessel of the patient to withdraw blood therefrom.

25. The method of claim 18 wherein step (b) comprises:
inserting a flexible angiocatheter into a blood vessel of the patient to withdraw blood therefrom.

26. A method of performing transluminal balloon angioplasty using a balloon angioplasty catheter having a proximal end, a distal end and at least one lumen extending through the catheter and opening distal to the balloon to permit fluid passing through the lumen to exit the catheter distal to the balloon, said method comprising:
a) inserting a dual lumen introducer sheath into a blood vessel, said dual lumen introducer sheath having a first lumen for insertion of the angioplasty catheter therethrough into the blood vessel and a second lumen for withdrawal of blood from the blood vessel;
b) inserting the distal end of the angioplasty catheter into the blood vessel through the catheter introduction lumen of the dual lumen introducer sheath and advancing said angioplasty catheter to a desired operative location;
c) providing an extracorporeal blood oxygenation device having a blood inlet and blood outlet;
d) fluidly connecting the blood withdrawal lumen of the dual lumen introducer sheath to the blood inlet of the extracorporeal oxygenation device;
e) fluidly connecting the blood outlet of the extracorporeal oxygenation device to the perfusion lumen fluid of the angioplasty catheter; and
f) withdrawing blood through the blood withdrawal lumen of the dual lumen introducer sheath and pumping the withdrawn blood through the extracorporeal oxygenation device and subsequently through the lumen of the catheter and out of the distal opening thereof.

27. The method of claim 26 step (a) further comprises:
inserting a dual lumen introducer sheath into a femoral artery of the patient.

28. The method of claim 26 wherein step (a) further comprises:
inserting a dual lumen introducer sheath into a axillary artery of the patient.

29. The method of claim 26 further comprising the step of:

adjusting the temperature of the blood prior to passage of the blood through the lumen of the catheter.

30. The method of claim 26 wherein step (b) comprises:
inserting an intravenous needle into a peripheral blood vessel of the patient to withdraw blood therefrom.

31. The method of claim 26 wherein step (b) comprises:
inserting a flexible intravascular cannula into a blood vessel of the patient to withdraw blood therefrom.

32. The method of claim 26 wherein step (b) comprises:
inserting a flexible angiocatheter into a blood vessel of the patient to withdraw blood therefrom.

33. A system for maintaining hemoperfusion during transluminal angioplasty procedures, said system comprising:
a balloon angioplasty catheter having a distal end, a proximal end and a perfusion lumen extending longitudinally therethrough an opening distal to the balloon such that perfusion fluid flowing through the perfusion fluid lumen may exit the catheter distal to the balloon;
an extracorporeal blood oxygenation device fluidly connected to the perfusion fluid lumen of the angioplasty catheter such that oxygenated blood exiting the blood oxygenation device will pass through the perfusion fluid lumen and will exit the catheter distal to the balloon; and
a pump for pumping blood through the extracorporeal blood oxygenation device and subsequently through the perfusion fluid lumen of the catheter.

34. The system of claim 33 further comprising:
an intravascular cannula insertable into the vasculature of the patient and fluidly connectable to the blood pump such that blood may be withdrawn from the patient, pumped through the extracorporeal blood oxygenation device and subsequently reinfused into the patient through the perfusion fluid lumen of the angioplasty catheter.

35. A system for maintaining hemoperfusion during transluminal angioplasty procedures, said system comprising:
a balloon angioplasty catheter having a distal end, a proximal end and a perfusion lumen extending longitudinally therethrough an opening distal to the balloon such that perfusion fluid flowing through the perfusion fluid lumen may exit the catheter distal to the balloon;
an extracorporeal blood oxygenation device fluidly connected to the perfusion fluid lumen of the angioplasty catheter such that oxygenated blood exiting the blood oxygenation device will pass through the perfusion fluid lumen and will exit the catheter distal to the balloon;
a pump for pumping blood through the extracorporeal blood oxygenation device and subsequently through the perfusion fluid lumen of the catheter; and
a dual lumen introducer sheath having a first lumen through which the angioplasty catheter is insertable and a second lumen through which blood may be withdrawn, said second lumen being connectable to the pump such that blood may be withdrawn from the patient through the second lumen, passed through the extracorporeal blood oxygenation device and subsequently reinfused into the patient through the perfusion lumen of the angioplasty catheter.

36. The system of claim 35 wherein said dual lumen introducer sheath comprises:
an outer tube having a proximal end and a distal end;
an inner tube disposed coaxially within said outer tube and defining an annular blood withdrawal space therebetween;
a hub formed on the proximal ends of said inner and outer tubes, said hub having a generally hollow inner bore which opens into the lumen of the inner tube to permit passage of the angioplasty catheter therethrough; and
a blood withdrawal sidearm having an inner bore which opens into the blood withdrawal space to permit withdrawal of blood from said blood withdrawal space.

37. A method of maintaining myocardial perfusion during coronary balloon angioplasty procedures wherein an angioplasty balloon causes substantial occlusion of a coronary artery, said method comprising:
a) withdrawing blood from the patient at a rate of 30-60 ml/min.;
b) providing an extracorporeal membrane oxygenator which is sized and configured to operate with a bloodflow rate of 30-60 ml/min. and to substantially raise the $P_{O_2}$ of blood flowing therethrough at such flow rate to a $P_{O_2}$ which is above normal arterial blood $P_{O_2}$;
c) passing the withdrawn blood through the extracorporeal membrane oxygenator at 30-60 ml/min. and causing said blood to be oxygenated to a $P_{O_2}$ above normal arterial $P_{O_2}$; and
d) reinfusing the oxygenated blood through the angioplasty catheter and causing the oxygenated blood to exit the angioplasty catheter distal to the occlusive balloon.

38. A method of decreasing the volume of perfusion blood necessary to maintain adequate myocardial perfusion during a coronary balloon angioplasty procedure wherein the angioplasty balloon causes substantial occlusion of a coronary artery, said method comprising:
passing a quantity of perfusion blood through an extracorporeal blood oxygenation device to raise to $P_{O_2}$ of said perfusion blood above normal arterial blood $P_{O_2}$; and
passing the oxygenated perfusion blood through the angioplasty catheter and causing the oxygenated perfusion blood to exit the angioplasty catheter distal to the occlusive balloon.

39. A method of providing a flow of extracorporeally oxygenated blood through a balloon angioplasty catheter, said method comprising the steps of:
inserting a dual lumen cannula into a blood vessel; said dual lumen cannula having a first catheter introducer passageway for insertion of the angioplasty catheter therethrough and a second blood withdrawal passageway for withdrawal of blood therethrough;
inserting an angioplasty catheter into the vasculature of the patient through the catheter introducer passageway of the dual lumen introducer cannula;
fluidly connecting the blood withdrawal passageway of the dual lumen introducer cannula to an extracorporeal membrane oxygenation device;
withdrawing blood from the blood vessel through the blood withdrawal passageway and passing the withdrawn blood through the extracorporeal oxygenation device for oxygenation therein; and
passing the oxygenated blood through a lumen of the catheter and causing the oxygenated blood to exit the catheter distal to the angioplasty balloon.

* * * * *